United States Patent [19]
Lee et al.

[11] Patent Number: 5,532,220
[45] Date of Patent: Jul. 2, 1996

[54] GENETIC MECHANISMS OF TUMOR SUPPRESSION

[75] Inventors: Wen-Hwa Lee; Phang-Lang Chen, both of San Diego, Calif.

[73] Assignee: The Regents of the University of California, Oakland, Calif.

[21] Appl. No.: 337,851

[22] Filed: Nov. 14, 1994

Related U.S. Application Data

[60] Continuation of Ser. No. 947,359, Sep. 18, 1992, abandoned, which is a division of Ser. No. 573,405, Aug. 24, 1990, abandoned, which is a continuation-in-part of Ser. No. 91,547, Aug. 31, 1987, Pat. No. 5,011,773, and a continuation-in-part of Ser. No. 108,748, Oct. 15, 1987, abandoned, and a continuation-in-part of Ser. No. 265,829, Oct. 31, 1988, abandoned, and a continuation-in-part of Ser. No. 533,892, Jul. 16, 1990, Pat. No. 5,104,571, and a continuation-in-part of Ser. No. 553,905, Jul. 16, 1990, abandoned.

[51] Int. Cl.$^6$ .......................... A61K 31/70; A61K 48/00; C12N 15/00; C12N 5/00
[52] U.S. Cl. ................. 514/44; 435/172.3; 435/240.2; 435/320.1; 424/93.21; 935/62; 935/57; 935/70
[58] Field of Search ........................ 514/44; 435/172.3, 435/240.2, 320.1, 317.1; 424/93.21; 935/62, 57, 70, 111; 800/DIG. 2

[56] References Cited

U.S. PATENT DOCUMENTS 4,497,796  2/1985  Salser et al. .

FOREIGN PATENT DOCUMENTS

| 0390323A2 | 2/1990 | European Pat. Off. . |
| 0518650A2 | 6/1992 | European Pat. Off. . |
| WO91/15580 | 10/1991 | WIPO . |

OTHER PUBLICATIONS

Anderson, W. French, "Prospects for Human Gene Therapy." *Science* 246:401–409 (1984).
Angier, N., "Light Cast on a Darkling Gene." *Discover* Mar.:85–96 (1987).
Banks et al., "Isolation of human–p53–specific monoclonal antibodies and their use in the studies of human p53 expression." *Eur. J. Biochem.* 159:529–534 (1986).
Bookstein et al., "Human retinoblastoma susceptibility gene: Genomic organization and analysis of heterozygous intragenic deletion mutants." *Proc. Natl. Acad. Sci. USA* 85:2210–2214 (1988).
Bookstein et al., "Suppression of Tumorigenicity of Human Prostate Carcinoma Cells by Replacing a Mutated RB Gene." *Science* 247:712–715 (1990).
Cattoretti et al., "Vimentin and p53 expression on epidermal growth factor receptor–positive, oestrogen receptor–negative breast carcinomas." *Br. J. Cancer* 57:353–357 (1988).
Cepko et al., "Construction and Applications of a Highly Transmissible Murine Retrovirus Shuttle Vector." *Cell* 37:1053–1062 (1984).
Chen et al., "Phosphorylation of the Retinoblastoma Gene Product Is Modulated during the Cell Cycle and Cellular Differentiation." *Cell* 58:1193–1198 (1989).
David et al., "Inactivation of the p53 oncogene by internal deletion or retroviral integration in erythroleukemic cell lines induced by Friend leukemia virus." *Oncogene* 3:179–185 (1988).
Dyson et al., "The Human Pailloma virus–16 E7 Oncoprotein Is Able to Bind to the Retinoblastoma Gene Product." *Science* 243:934–937 (1989).
Eliyahu et al., "Wild–type p53 can inhibit oncogene–mediated focus formation." *Proc. Natl. Acad. Sci USA* 86:8763–8767 (1989).
Finlay et al., "The p53 Proto–Oncogene Can Act as a Suppressor of Transformation." *Cell* 57:1083–1093 (1989).
Friedmann, Theodore, "Gene Therapy of Cancer through Restoration of Tumor–Suppressor Functions?" *Cancer* 70:1810–1817 (1992).
Friend et al., "Deletions of a DNA sequence in retinoblastoma and mesenchymal tumors: Organization of the sequence and its encoded protein." *Proc. Natl. Acad. Sci. USA* 84:9059–9063 (1987).
Friend et al., "A human DNA segment with properties of the gene that predisposes to retinoblastoma and osteosarcoma." *Nature* 323:643–646 (1986).
Fung et al., "Structural Evidence for the Authenticity of the Human Retinoblastoma Gene." *Science* 236:1657–1661 (1987).
Gossler et al., "Transgenesis by means of blastocyst–derived embryonic stem cell lines." *Proc. Natl. Acad. Sci. USA* 83:9065–9069 (1986).
Harlow et al., "Molecular Cloning and In Vitro Expression of a cDNA Clone for Human Cellular Tumor Antigen p53." *Molecular and Cellular Biol.* 5(7):1601–1610 (1985).
Harris, Henry, "Malignant tumours generated by recessive mutations." *Nature* 323:582–583 (1986).
Harris et al., "Molecular Basis for Heterogeneity of the Human p53 Protein." *Molecular and Cellular Biol.* 6(12) 4650–4656 (1986).
Hong et al., "Structure of the human retinoblastoma gene." *Proc. Natl. Acad. Sci. USA* 86:5502–5506 (1989).
Hooper et al., "HPRT–deficient (Lesch–Nyhan) mouse embryos derived from germline colonization by cultured cells." *Nature* 326:292–295 (1987).
Hu et al., "The regions of the retinoblastoma protein needed for binding to adenovirus E1A or SV40 large T antigen are common sites for mutations." *The EMBO Journal* 9(4):1147–1155 (1990).
Huang et al., "Suppression of the Neoplastic Phenotype by Replacement of the RB Gene in Human Cancer Cells." *Science* 242:1563–1566 (1988).
Huang et al., "A cellular protein that competes with SV40 T antigen for binding to the retinoblastoma gene product." *Nature* 350:160–162 (1991).

(List continued on next page.)

Primary Examiner—Jasemine C. Chambers
Attorney, Agent, or Firm—Campbell and Flores

[57] ABSTRACT

A method for utilizing p53 cDNA, and p53 gene products for the suppression of the neoplastic phenotype.

6 Claims, 9 Drawing Sheets

OTHER PUBLICATIONS

Huang et al., "Two distinct and frequently mutated regions of retinoblastoma protein are required for binding to SV40 T antigen." *The EMBO Journal* 9(6):1815–1822 (1990).

Kantoff et al., "Correction of adenosine deaminase deficiency in cultured human T and B cells by retrovirus-mediated gene transfer." *Proc. Natl. Acad. Sci. USA* 83:6563–6567 (1986).

Kopelovich and DeLeo, "Elevated Levels of p53 Antigen in Cultured Skin Fibroblasts and Patients with Hereditary Adenocarcinoma of the Colon and Rectum and its Relevance to Oncogenic Mechanisms." *JNCI* 77(6):1241–1244 (1986).

Kuehn et al., "A potential animal model for Leshc-Nyhan syndrome through introduction of HPRT mutations into mice." *Nature* 326:295–298 (1987).

Lamb et al., "Characterization of Human p53 Gene." *Molecular and Cellular Biol.* 6(5):1379–1385 (1986).

Lane et al., "p53: oncogene: or anti-oncogene?" *Genes & Development* 4:1–8 (1990).

Lavigueur et al., "High Incidence of Lung, Bone, and Lymphoid Tumors in Transgenic Mice Overexpressing Mutant Alleles of the p53 Oncogene." *Mol. & Cell. Bio.* 9(9):3982–3991 (1989).

Lee et al., "Inactivation of the Retinoblastoma Susceptibility Gene in Human Breast Cancers." *Science* 241:218–221 (1988).

Lee et al., "Molecular cloning of the human esterase D gene, a genetic marker of retinoblastoma." *Proc. Natl. Acad. Sci. USA* 83:6337–6341 (1986).

Lee et al., "Molecular mechanism of retinoblastoma gene inactivation in retinoblastoma cell line Y79." *Proc. Natl. Acad. Sci. USA* 85:6017–6021 (1988).

Lee et al., "Human Retinoblastoma Susceptibility Gene: Cloning, Identification, and Sequence." *Science* 235:1394–1399 (1987).

Lee et al., "Purification, biochemical characterization, and biological function of human esterase D." *Proc. Natl. Acad. Sci. USA* 83:6790–6794 (1986).

Lee et al., "The retinoblastoma susceptibility gene encodes a nuclear phosphoprotein associated with DNA binding activity." *Nature* 329:642–645 (1987).

Lübbert et al., "p53 in chronic myelogenous leukemia." *J. Exp. Med.* 167:873–886 (1988).

Ludlow et al., "SV40 Large T Antigen Binds Preferentially to an Underphosphorylated Member of the Retinoblastoma Susceptibility Gene Product Family." *Cell* 56:57–65 (1989).

Mann et al., "Construction of a Retrovirus Packaging Mutant and Its Use to Produce Helper-Free Defective Retrovirus." *Cell* 33:153–159 (1983).

Matlashewski et al., "Isolation and characterization of a human p53 cDNA clone: expression of the human p53 gene." *EMBO J.* 3(13):3257–3262 (1984).

Mercer et al., "Microinjection of monoclonal antibody to protein p53 inhibits serum-induced DNA synthesis in 3T3 cells." *Proc. Natl. Acad. Sci. USA* 79:6309–6312 (1982).

Mercer et al., "Negative growth regulation in a glioblastoma tumor cell line that conditionally expresses human wild-type p53." *Proc. Natl. Acad. Scie USA* 87:6166–6170 (1990).

Miller et al., "Generation of Helper-Free Amphotropic Retroviruses That Transduce a Dominant-Acting, Methotrexate-Resistant Dihydrofolate Reductase Gene." *Molecular and Cellular Biol.* 5(3):431–437 (1985).

Miller et al., "Transfer of Genes into Human Somatic Cells Using Retrovirus Vectors." *Cold Spring Harbor Symposia on Quantitative Biology* LI:1013–1019 (1986).

Miller et al., "A transmissible retrovirus expressing human hypoxanthine phosphoribosyltransferase (HPRT): Gene transfer into cells obtained from humans deficient in HPRT." *Proc. Natl. Acad. Sci. USA* 80:4709–4713 (1983).

Mowat et al., "Rearrangements of the cellular p53 gene in erythroleukaemic cells transformed by Friend virus." *Nature* 314:633–636 (1985).

Munroe et al., "Loss of a highly conserved domain on p53 as a result of gene deletion during Friend virus-induced erythroleukemia." *Oncogene* 2:621–624 (1988).

Murphree et al., "Retinoblastoma: Clues to Human Oncogenesis." *Science* 223:1028–1033 (1984).

Nicolau et al., "Liposomes as Carriers for in Vivo Gene Transfer and Expression." *Methods in Enzymology* 144:157–176.

Nigro, Janice, "Mutations in the p53 gene occur in diverse human tumour types." *Nature* 342:705–708 (1989).

Parada et al., "Cooperation between gene encoding p53 tumour antigen and ras in cellular transformation." *Nature* 312:649–651 (1984).

Prokocimer et al., "Expression of p53 in human leukemia and lymphoma." *Blood* 68(1):113–118 (1986).

Rovinski et al., "Deletion of 5'-coding Sequences of the Cellular p53 Gene in Mouse Erythroleukemia: a Novel Mechanism of Oncogene Regulation." *Mol. & Cell. Biol.* 7(2):847–853 (1987).

Sager, Ruth, "Tumor Suppressor Genes: The Puzzle and the Promise." *Science* 246:1406–1412 (1989).

Shew et al., "Antibodies Detecting Abnormalities of the Retinoblastoma Susceptibility Gene Product (pp110$^{RB}$) in Osteosarcomas and Synovial Sarcomas." *Oncogene Research* 1:205–214 (1989).

Shew et al., "C-terminal truncation of the retinoblastoma gene product leads to functional inactivation." *Proc. Natl. Acad. Sci. USA* 87:6–10 (1990).

Shohat et al., "Inhibition of cell growth mediated by plasmids encoding p53 anti-sense." *Oncogene* 1:277–283 (1987).

Smith et al., "Expression of the p53 oncogene in acute myeloblastic leukemia," *J. Exp. Med.* 164:751–761 (1986).

Soussi et al., "Cloning and characterization of a cDNA from *Xenopus laevis* coding for a protein homologous to human and murine p53." *Oncogene* 1(1):71–78 (1987).

Thomas et al., "High Frequency Targeting of Genes to Specific Sites in the Mammalian Genome." *Cell* 44:419–428 (1986).

Weinberg, Robert, "Positive and Negative Controls on Cell Growth." *Biochemistry* 28(21):8263–8269 (1989).

Weissman et al., "Introduction of a Normal Human Chromosome 11 into a Wilms' Tumor Cell Line Controls Its Tumorigenic Expression." *Science* 236:175–180 (1987).

Wills et al., "Development and Characterization of Recombinant Adenoviruses Encoding Human p53 for Gene Therapy of Cancer." *Human Gene Therapy* 5:1079–1088 (1994).

Wolf et al., "In Vitro Expression of Human p53 cDNA Clones and Characterization of the Cloned Human p53 Gene." *Molecular and Cellular Biol.* 5(8):1887–1893 (1985).

Zakut–Houri et al., "Human p53 cellular tumor antigen: cDNA sequence and expression in COS cells." *The EMBO Journal* 4(5):1251–1255 (1985).

Figure 8

```
1/1                                    31/11
ATG GAG GAG CCG CAG TCA GAT CCT AGC GTC GAG CCC CCT CTG AGT CAG GAA ACA TTT TCA
61/21                                  91/31
GAC CTA TGG AAA CTA CTT CCT GAA AAC AAC GTT CTG TCC CCC TTG CCG TCC CAA GCA ATG
121/41                                 151/51
GAT GAT TTG ATG CTG TCC CCG GAC GAT ATT GAA CAA TGG TTC ACT GAA GAC CCA GGT CCA
181/61                                 211/71
GAT GAA GCT CCC AGA ATG CCA GAG GCT GCT CCC CGC GTG GCC CCT GCA CCA GCA GCT CCT
241/81                                 271/91
ACA CCG GCG GCC CCT GCA CCA GCC CCC TCC TGG CCC CTG TCA TCT TCT GTC CCT TCC CAG
301/101                                331/111
AAA ACC TAC CAG GGC AGC TAC GGT TTC CGT CTG GGC TTC TTG CAT TCT GGG ACA GCC AAG
361/121                                391/131
TCT GTA ACT TGC ACG TAC TCC CCT GCC CTC AAC AAG ATG TTT TGC CAA CTG GCC AAG ACC
421/141                                451/151
TGC CCT GTG CAG CTG TGG GTT GAT TCC ACA CCC CCG CCC GGC ACC CGC GTC CGC GCC ATG
481/161                                511/171
GCC ATC TAC AAG CAG TCA CAG CAC ATG ACG GAG GTT GTG AGG CGC TGC CCC CAC CAT GAG
541/181                                571/191
CGC TGC TCA GAT AGC GAT GGT CTG GCC CCT CCT CAG CAT CTT ATC CGA GTG GAA GGA AAT
601/201                                631/211
TTG CGT GTG GAG TAT TTG GAT GAC AGA AAC ACT TTT CGA CAT AGT GTG GTG GTG CCC TAT
661/221                                691/231
GAG CCG CCT GAG GTT GGC TCT GAC TGT ACC ACC ATC CAC TAC AAC TAC ATG TGT AAC AGT
721/241                                751/251
TCC TGC ATG GGC GGC ATG AAC CGG AGA CCC ATC CTC ACC ATC ATC ACA CTG GAA GAC TCC
781/261                                811/271
AGT GGT AAT CTA CTG GGA CGG AAC AGC TTT GAG GTG CGT GTT TGT GCC TGT CCT GGG AGA
841/281                                871/291
GAC CGG CGC ACA GAG GAA GAG AAT CTC CGC AAG AAA GGG GAG CCT CAC CAC GAG CTG CCC
901/301                                931/311
CCA GGG AGC ACT AAG CGA GCA CTG CCC AAC AAC ACC AGC TCC TCT CCC CAG CCA AAG AAG
961/321                                991/331
AAA CCA CTG GAT GGA GAA TAT TTC ACC CTT CAG ATC CGT GGG CGT GAG CGC TTC GAG ATG
1021/341                               1051/351
TTC CGA GAG CTG AAT GAG GCC TTG GAA CTC AAG GAT GCC CAG GCT GGG AAG GAG CCA GGG
1081/361                               1111/371
GGG AGC AGG GCT CAC TCC AGC CAC CTG AAG TCC AAA AAG GGT CAG TCT ACC TCC CGC CAT
1141/381                               1171/391
AAA AAA CTC ATG TTC AAG ACA GAA GGG CCT GAC TCA GAC TGA
```

Figure 9

```
1/1                                 31/11
Met Glu Glu Pro Gln Ser Asp Pro Ser Val Glu Pro Pro Leu Ser Gln Glu Thr Phe Ser
61/21                               91/31
Asp Leu Trp Lys Leu Leu Pro Glu Asn Asn Val Leu Ser Pro Leu Pro Ser Gln Ala Met
121/41                              151/51
Asp Asp Leu Met Leu Ser Pro Asp Asp Ile Glu Gln Trp Phe Thr Glu Asp Pro Gly Pro
181/61                              211/71
Asp Glu Ala Pro Arg Met Pro Glu Ala Ala Pro Arg Val Ala Pro Ala Pro Ala Ala Pro
241/81                              271/91
Thr Pro Ala Ala Pro Ala Pro Ala Pro Ser Trp Pro Leu Ser Ser Ser Val Pro Ser Gln
301/101                             331/111
Lys Thr Tyr Gln Gly Ser Tyr Gly Phe Arg Leu Gly Phe Leu His Ser Gly Thr Ala Lys
361/121                             391/131
Ser Val Thr Cys Thr Tyr Ser Pro Ala Leu Asn Lys Met Phe Cys Gln Leu Ala Lys Thr
421/141                             451/151
Cys Pro Val Gln Leu Trp Val Asp Ser Thr Pro Pro Gly Thr Arg Val Arg Ala Met
481/161                             511/171
Ala Ile Tyr Lys Gln Ser Gln His Met Thr Glu Val Val Arg Arg Cys Pro His His Glu
541/181                             571/191
Arg Cys Ser Asp Ser Asp Gly Leu Ala Pro Pro Gln His Leu Ile Arg Val Glu Gly Asn
601/201                             631/211
Leu Arg Val Glu Tyr Leu Asp Asp Arg Asn Thr Phe Arg His Ser Val Val Val Pro Tyr
661/221                             691/231
Glu Pro Pro Glu Val Gly Ser Asp Cys Thr Thr Ile His Tyr Asn Tyr Met Cys Asn Ser
721/241                             751/251
Ser Cys Met Gly Gly Met Asn Arg Arg Pro Ile Leu Thr Ile Ile Thr Leu Glu Asp Ser
781/261                             811/271
Ser Gly Asn Leu Leu Gly Arg Asn Ser Phe Glu Val Arg Val Cys Ala Cys Pro Gly Arg
841/281                             871/291
Asp Arg Arg Thr Glu Glu Glu Asn Leu Arg Lys Lys Gly Glu Pro His His Glu Leu Pro
901/301                             931/311
Pro Gly Ser Thr Lys Arg Ala Leu Pro Asn Asn Thr Ser Ser Ser Pro Gln Pro Lys Lys
961/321                             991/331
Lys Pro Leu Asp Gly Glu Tyr Phe Thr Leu Gln Ile Arg Gly Arg Glu Arg Phe Glu Met
1021/341                            1051/351
Phe Arg Glu Leu Asn Glu Ala Leu Glu Leu Lys Asp Ala Gln Ala Gly Lys Glu Pro Gly
1081/361                            1111/371
Gly Ser Arg Ala His Ser Ser His Leu Lys Ser Lys Lys Gly Gln Ser Thr Ser Arg His
1141/381                            1171/391
Lys Lys Leu Met Phe Lys Thr Glu Gly Pro Asp Ser Asp Opa
```

GENETIC MECHANISMS OF TUMOR SUPPRESSION

This invention was made with Government support under Grant No. EY05758 with the National Institute of Health, and the University of California. The Government has certain rights in this invention.

This application is a continuation of application Ser. No. 07/947,359, filed Sep. 18, 1992 now abandoned; which is a divisional of U.S. Ser. No. 07/573,405 filed Aug. 24, 1990 now abandoned; which is a continuation-in-part of U.S. Ser. No. 07/091,547 filed Aug. 31, 1987 (patent issued: U.S. Pat. No. 5,011,773); and a continuation-in-part of Ser. No. 07/108,748 filed Oct. 15, 1987 now abandoned; and a continuation-in-part of Ser. No. 07/265,829 filed Oct. 31, 1988 (abandoned); and a continuation-in-part of Ser. No. 07/533,892 filed Jul. 16, 1990, and a continuation-in-part of U.S. Ser. No. 07/553,905 filed Jul. 16, 1990 now abandoned.

TECHNICAL FIELD

This invention relates in general to cell therapy and to methods for treating cells to suppress tumorigenesis.

BACKGROUND ART

Much of the focus of cancer research has been on the diagnosis and treatment of the condition. In recent years, because of advances in knowledge of biochemical processes at the cellular and subcellular levels, attention has been directed to methods, not only for diagnosing and treating cancer, but also for discovering a predisposition for cancer in the organism.

In these studies, "cancer suppression" was originally defined by a loss of tumorigenicity observed in fusion cells made with tumor cells and normal fibroblasts, lymphocytes or keratinocytes. The effect was presumed to be mediated by dominant suppressive factors in normal cells. Evidence indicated that these factors were in part genetic since a correlation existed between suppression of tumorogenicity and the presence of certain chromosomes in fused cells.

Another meaning for cancer suppressing genes arose in connection with genetic studies on certain childhood neoplasms and adult tumor syndromes. Genes contributing to the formation of these tumors appear to be oncogenic by loss of function, rather than activation, as with the classical oncogenes. Retinoblastoma, a childhood eye cancer, has provided the prototypic example. Refined cytogenic analysis and study of restriction fragment length polymorphisms (RFLPs) have suggested that retinoblastoma may result from a loss of a gene locus located in chromosome band 13q14. As referenced to the above referenced pending patent applications will disclose, significant advances have been made in the utilization of RB cDNA and RB protein not only in diagnosis and methods of treatment of RB-related tumors, but also in the elucidation of the cancer suppressor functions of other genes. Nevertheless, a significant need exists for appropriate methods for the therapeutic treatment of osteosarcoma, lung carcinoma, lymphomas and leukemias, which are not aminable to treatment by RB modalities.

In view of the above, it would be highly desirable to have a method for specific therapeutic treatment, independent of RB modalities, for osteosarcomas, lung carcinomas, lymphomas and leukemias. Further, it would be highly desirable to have such methods which could be used in conjunction with RB cDNA and protein product for the treatment of various tumors. Of course, it would be highly desirable to have such a therapeutic product which could be made in a purified state and which would be readily and effectively deliverable to a defective cell in a safe manner.

DISCLOSURE OF INVENTION

It is a primary object of this invention to provide generally safe and specific therapeutic methods and products useful for controlling cancer suppression. It is a further object of this invention to provide products and methods for controlling cancer suppression which are specific for suppression and eradication of cancer tumors and which utilize biotechnological methods and products.

It is a still further object of the present invention to provide a pharmaceutical composition for therapeutically treating cancers wherein the composition is functional at the cellular and intracellular levels.

It is yet still another object of the present invention to provide a pharmaceutical composition for treating conditions caused by defective, mutant or absent cancer suppressor genes wherein the active ingredient of the composition is a natural or synthetically produced product.

The present invention provides a method for utilizing p53 cDNA, and p53 gene products, for the suppression of the neoplastic phenotype.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein:

FIG. 8 is the nucleotide sequence of the p53 gene.

FIG. 9 is the amino acid sequence of the p53 protein.

DETAILED DESCRIPTION OF THE FIGURES

Figure 1A:
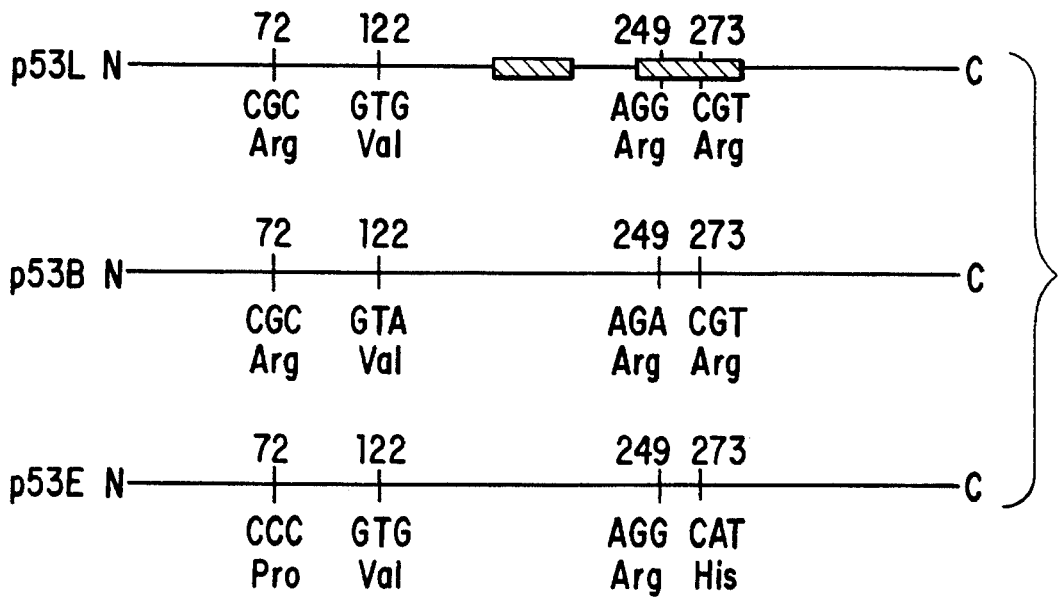
FIG. 1A is a diagrammatic representation of three human p53cDNAs.

In FIG. 1A, three human p53 cDNAs are diagrammed. The sequence reported by Lam and Crawford, *Mol. Cell. Biol.* 6, 1379–1385 (1986), here labelled as p53L, was derived by sequencing clones from human fetal liver cDNA and genomic libraries, and is considered to be wild-type. p53B is a cDNA clone derived from fetal brain RNA by the RT-PCR method which resulted in cloning of wild type p53 (p53B) cDNA as follows: about 15 µg of fetal brain RNA were mixed with 1.5 µg of oligo (dT) primer and 60 units of avian myeloblastosis virus reverse transcriptase in cDNA buffer (50 mM Tris-HCl, pH 8.0, 80 mM KCl, 5 mM MgCl2, 1 mM each dATP, dGTP, dTTP, and dCTP). The reaction mixture was incubated for 90 min at 42° C. After reaction, RNA was degraded with 0.5N NaOH, and single-stranded cDNA was precipitated with ethanol. PCR amplification was carried out with one-tenth of the cDNA, 100 ng of each oligonucleotide primer (5'-TGCAAGCTTTCCACGACG-GTGACACGCT-3' and 5'-AGTGCAGGCCA-ACTTGT-TCAGTGGA-3'), and 5U of Taq polymerase in PCR buffer (50 mM KCl, 10 mM Tris-HCl, pH 8.3, 1.5 mM MgCl2, and 0.001% gelatin) for 40 cycles in a programmable heat block (Ericomp, San Diego, Calif.). Each cycle included denaturation at 93° C. for 1 minute, reannealing at 62° C. for 80 seconds, and primer extention at 72° C. for 3 minutes. PCR products were extracted with phenol and precipitated with ethanol. The precipitate was dissolved in $H_2O$ and digested with restriction enzymes (Hind III and Sma 1). The p53cDNA fragment was subcloned into virus vector to form Vp53B-Neo. Subcloned p53B was sequenced by using the dideoxy chain termination method (F. Sanger, S. Nicklen, A. R. Coulsen, *Proc. Natl. Acad. Sci, U.S.A.* 74, 5463 (1977)).

The deducted amino acid sequences of p53B and p53L were identical despite two silent nucleotide substitutions as indicated. p53E is a cDNA clone provided by E. Harlow, that has amino acid substitutions at positions 72 and 273 relative to p53L or p53B. The Arg/Pro$^{72}$ replacement represents a common amino acid polymorphism, without known functional significance. On the other hand, the substitution of His for Arg at position 273 is found exclusively in tumor cells and is considered to be a mutation. Like many other p53 mutations, Arg $^{273}$→His lies within one of two regions required for binding to SV40 T antigen (hatched boxes).

Figure 1B:
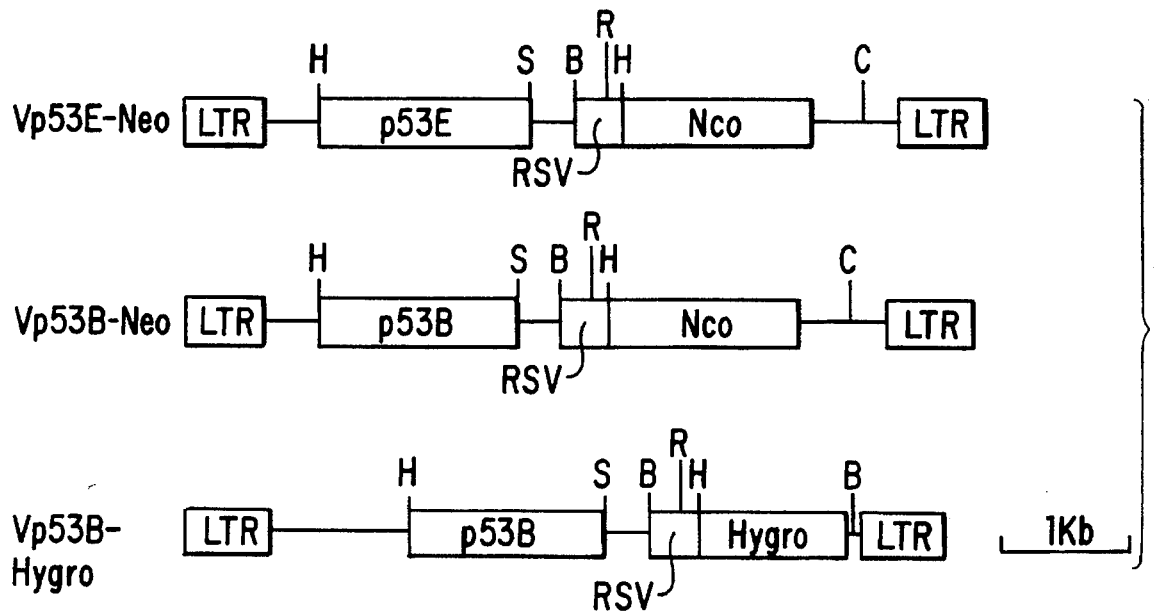
FIG. 1B is a diagrammatic representation of the genomic organization of three p53 retroviruses.

In FIG. 1B, the genomic organization of three p53 retroviruses are diagrammed. Vp53E-Neo was constructed by inserting a 1.5 kb Hind III-Sma I DNA fragment containing p53E into the plasmid pLRbRNL, replacing RB cDNA. A 1.35 kb p53B DNA obtained by RT-PCR was directly inserted into the pLRbRNL vector to form Vp53B-Neo. The insert in one clone was entirely sequenced, as diagrammed in FIG. 1A. Vp53B-Hygro was constructed by insertion of a Hind III DNA fragment containing p53B and the RSV promoter into plasmid 477 (a MuLV-Hygro vector kindly provided by W. Hammerschmidt and B. Sugden). These constructs were then used to produce the corresponding viral stocks using conventional techniques. Some major restriction sites important for construction are indicated. H=Hind III, R=EcoR I, S=Sma I, B - Bam HI, C=Cla I.

Figure 2B:
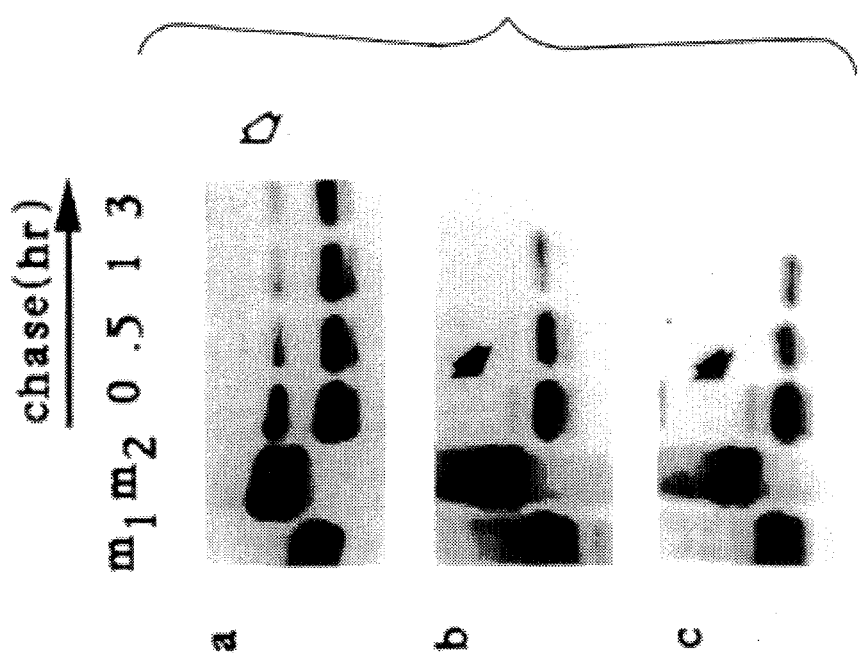
FIG. 2B is a chromatogram depicting half-life determination of human p53 in virus-producing lines by pulse-chase labeling experiments.
Figure 2A:
FIG. 2A is a chromatogram depicting expression of human p53 proteins in virus-producing cell lines.

FIG. 2A is a chromatogram depicting Murine PA 12 cells (Lane m1), human WERI-Rb27 retinoblastoma cells (Lane m2), and Vp53En-, Vp53BN-, or Vp53BH-producing PA 12 cells which were metabolically labelled with $^{35}$-methionine. Cell lysates were immunoprecipitated with anti-p53 antibody PAb421 utilizing conventional methods. Immunoprecipitates were separated by 8.5% SDS-polyacrylamide gel electrophoresis (SDS-PAGE), and autoradiographed. marker lanes m1 and m2 show endogenous murine p53 (Mp53) and both polymorphic forms of human p53 (Hp53). Human p53B (filled arrow) and p53E (open arrow) proteins in mouse cells are indicated.

FIG. 2B depicts half-life determination of human p53 in virus-producing lines by pulse-chase labeling experiments. PA12 cells expressing p53E (panel a) or p53B (panels b & c, representing two independent clones) were labelled with 0.25 mCi/ml $^{35}$S-methionine for 60 minutes, and chased with a 1000-fold molar excess of unlabeled methionine. At the indicated times, cells were harvested for immunoprecipitation of p53 protein with PAb421 as described above. The half-life of p53B was 20–30 minutes whereas that of p53E was 4–5 hours. Marker lanes m1 and m2, and filled and open arrows, were as in FIG. 2A.

FIG. 3 is a chromatogram depicting expression of human p53 proteins in virus-infected Saos-2 cells. Saos-2 cells (lanes 1 and 7) were infected with Vp53E-Neo, Vp53B-Neo, or Vp53B-Hygro to generate p53EN (lanes 2–6), p53BN (lanes 8–10), or p53BH (lanes 11 and 12) clones, respectively. Saos-2 cells were also doubly infected with Vp53E-Neo and Vp53B-Hygro to generate p53EN-BH clones (lanes 13–15). Randomly-selected clones, and WERI-Rb27 cells (lanes M), were labeled with $^{35}$S-methionine and immunoprecipitated with PAb421 as described with regard to FIG. 2A. p53B (filled arrows) and p53E (open arrows) are indicated.

Figure 4:
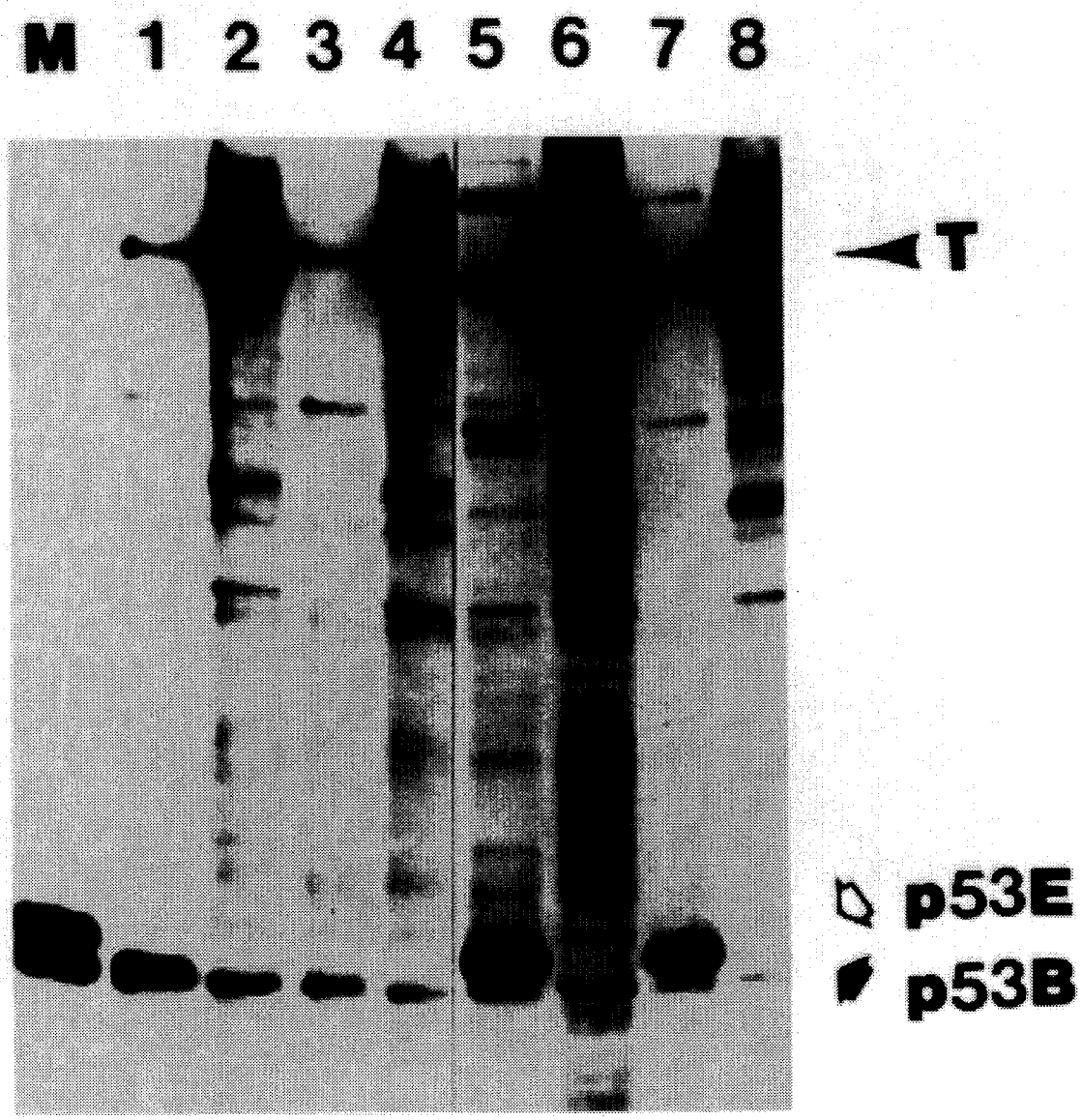
FIG. 4 is a chromatogram of p53B/T complex formation in Saos-2 cells.

FIG. 4 depicts p53B/T complex formation in Saos-2 cells. Clones p53BN-1 (lanes 1 and 2), p53BH-1 (lanes 3 and 4), p53EN-1-BH-1 (lanes 5 and 6), and p53EN-1-BH-2-(lanes 7 and 8) were transfected with plasmid pRSV40T by conventional methods, and 60 hours later, were metabolically labelled with $^{35}$S-methionine. Cell lysates were immunoprecipitated with PAb421 (lanes M, 1, 3, 5 and 7) or with PAb4 19, a monoclonal antibody against SV40T antigen (lanes 2, 4, 6 and 8). PAb419 coprecipitated only p53B in cells expressing both pS3B and p53E.

Figure 5A:
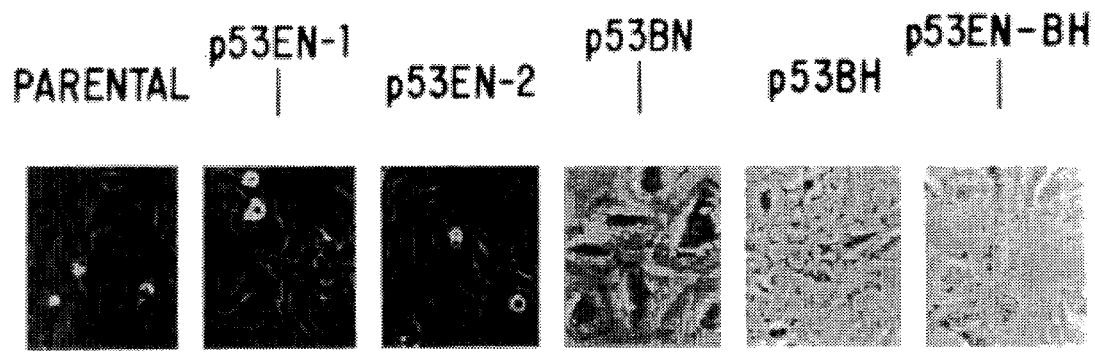
FIG. 5A and 5B depict morphology in a culture of parental Saos-2 cells.

FIG. 5 is a photograph depicting morphology in culture of parental Saos-2 cells, and representative virus-infected clones at magnification 100x. In row A, exponentially growing cells were shown while in row B, cells at confluency are shown.

Figure 6B:
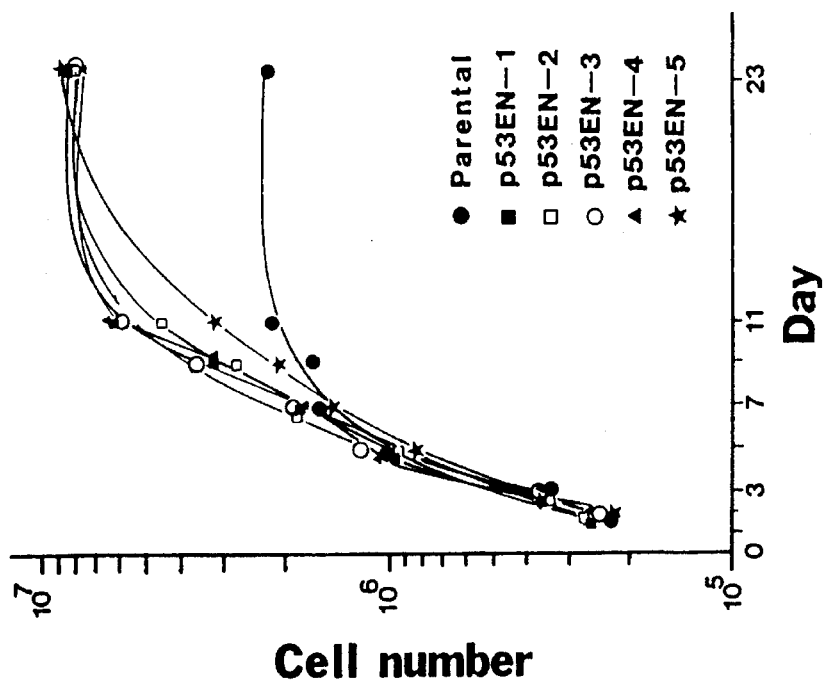
FIG. 6B is a schematic representation of the saturation density of parental Saos-2 and EN clones.
Figure 6A:
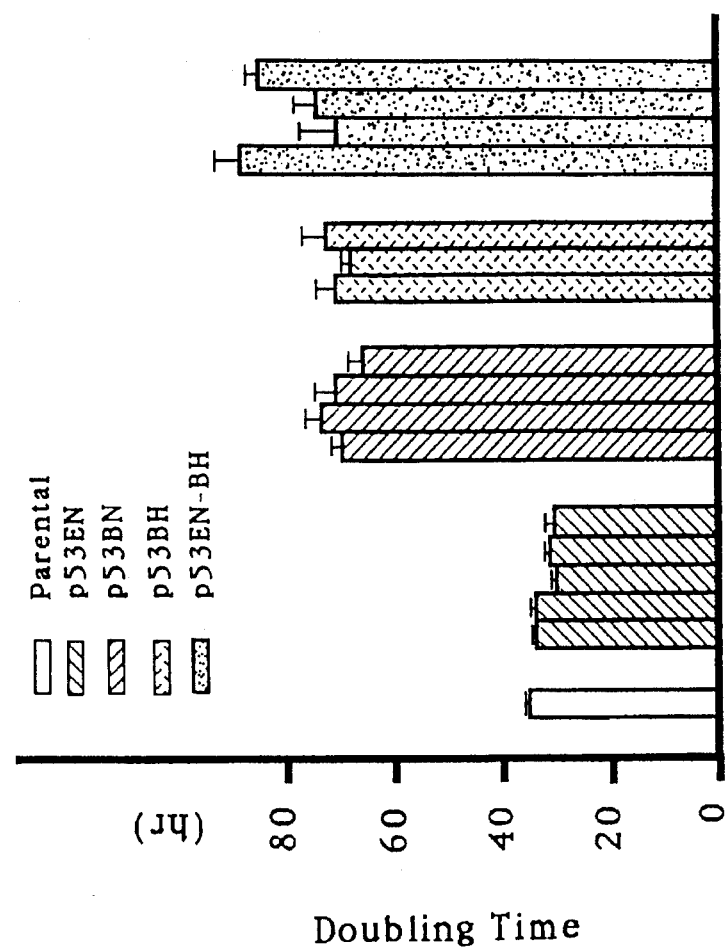
FIG. 6A is a schematic representation of the doubling times of parental Saos-2 cells and virus-infected clones.

FIGS. 6A and 6B are schematic representations of growth effects of p53 expression in Saos-2 cells. In FIG. 6a, the doubling times of parental Saos-2 cells and virus-infected clones in an exponential growth stage are shown. Equal numbers of each cell type were seeded into 60 mm culture dishes; cells of two dishes were trypsinized and counted at daily intervals for 4 days. Doubling times were derived from lines fitted to log cell numbers. FIG. 6B shows the saturation density of parental Saos-2 and En clones. Equal numbers ($1 \times 10^5$) of cells were seeded into 60 mm culture dishes; cells of two dishes were trypsinized and counted at the times indicated. Plotted points were mean cell numbers from duplicate dishes. Saturation density of p53E-expressing cells was 4- to 5- fold greater than parental cells.

FIG. 7 is a Southern blot of p53EN-BH cells which harbored one copy of Vp53E-Neo and one copy of Vp53B-Hygro. Genomic DNA (10 µg) extracted from parental Saos-2 cells and the indicated clones was digested with EcoR I, and separated in 0.7% agarose gels. Southern transfer was performed, and nylon membranes were hybridized with $^{32}$P-labelled neo (panel A) or hygro (panel B) DNA probes, utilizing standard methods. A single junctional fragment is seen in each clone with each probe, indicating single integrated copies of each virus.

BEST MODE FOR CARRYING OUT THE INVENTION

Tumor suppressor genes are defined as genes for which loss-of-function mutations are oncogenic. It is recognized that wild-type alleles of such genes may function to prevent or suppress oncogenesis. The retinoblastoma gene (RB) is the phototype of this class. Both alleles of this gene are invariably mutated in retinoblastoma cells, and RB mutations are also found in a subset of other human neoplasms including osteosarcoma, soft-tissue sarcomas, and carcinomas of breast, lung, bladder and prostate. Introduction of a wild-type copy of RB into retinoblastoma cells suppressed their tumorigenic properties in nude mice, thereby providing direct evidence for tumor suppression by a single gene. In this regard, please refer to the copending patent application entitled "Products and Methods for Controlling the Suppression of the Neoplastic Phenotype," Ser. No. 265,829, filed Oct. 31, 1988. The wild-type RB gene was also introduced into human prostate carcinoma cells containing an endogenous, mutated RB protein (*Science* 247, 712–715 (1990)). Expression of the exogenous gene again suppressed the tumorigenicity of these cells, implying that wild-type RB protein was phenotypically dominant to the mutated form. These results support a general model for the properties of tumor suppressor genes that has emerged from the "two-hit" hypothesis of Knudson and the cell hybrid studies of Harris et al. (*Proc. Natl. Acad. Sci. USA* 68, 820–823 (1971)); *Nature* 223, 363–368 (1969)). The nucleotide sequence of the p53 gene is depicted in FIG. 8.

p53 (FIG. 9) was originally identified as a mammalian cellular protein that binds to SV40T antigen, a property that is also shared by RB protein. Deletions or rearrangements of the murine or human gene encoding p53 were found in Friend virus-induced murine erythroleukemias, and in human osteosarcomas, lung carcinomas, lymphomas and leukemias. On the other hand, many human breast, lung and colon carcinomas expressed high levels of aberrant p53 species with markedly prolonged half-lives due to certain point mutations in the p53 gene (*Genes Devel.* 4, 1–8 (1990)). These observations suggest that mutation of p53 contributes to human oncogenesis. p53 was originally considered to be an oncogene because it was known that it could transform primary rat embryo fibroblasts in concert with an activated ras gene. However, the observation of p53 deletions, and point mutations scattered over several exons, also suggested that p53 might be a tumor suppressor gene, i.e., a gene that was inactivated by mutation. Indeed, Finlay et al. and Eliyahu et al. (*Cell* 57, 1083–1093 (1989)) *Proc. Natl. Acad. Sci U.S.A.* 86, 8763–8767 (1989)) found that cotransfection of murine wild-type p53 DNA could reduce the transformation efficiency of transfected oncogenes in rat embryo fibroblasts, whereas mutated p53 DNA enhanced such transformation. The dominant transforming effect was presumed to be due to a "dominant negative" activity of mutated p53 protein that somehow blocked the growth-restricting function of wild-type p53 protein in cells. This model suggested that the relative quantity of mutated to wild-type p53 could determine the transformed phenotype, but gene dosage could not be tightly controlled in these transfection studies.

Because of such technical questions, as well as the possibility of species-specific differences in p53 function and the uncertain relevance of transformed animal cells to human neoplasia, it was determined that the biological properties of p53 in the human system should be reassessed. It was recognized that an ideal host cell for these studies would allow the experimental manipulation of single copies of mutated or wild-type p53 alleles. However, most cultured human cells contain endogenous and possibly mutated p53 alleles that are not accessible to external control. The human osteosarcoma cell line Saos-2 was therefore chosen because it has no endogenous p53 due to complete deletion of its gene. Recombinant retroviruses derived from Moloney murine leukemia virus (Mo-MuLV) were used to introduce mutated and/or wild-type p53 under LTR promoter control. Cell clones isolated after infection and selection carried only a single integrated provirus of each type, and multiple clones were analyzed to exclude positional effects. A comprehensive assessment of biological properties of these clones included morphology, growth rates and saturation density in culture, colony formation in soft agar, and tumorigenicity in nude mice.

Preparation of Mutated and Wild-Type p53 Recombinant Retroviruses.

As a reference standard for human wild-type p53, the genomic DNA sequence of Lamb and Crawford (*Mol. Cell. Biol.* 6, 1379–1385 (1986)) was used. Potentially wild-type p53 cDNA was isolated from fetal brain RNA by the method of RT-PCR, and was cloned into plasmid. In cloning of wild type p53 (p53B) cDNA about 5 μg of fetal brain RNA were mixed with 1.5 μg of oligo(dT) primer and 60 units of avian myeloblastosis virus reverse transcriptase in cDNA buffer (50 mM Tris-HCl, pH 8.0, 80 mM KCl, 5 mM $MgCl_2$, 1 mM each dATP, dGTP, dTTP, and dCTP). The reaction mixture was incubated for 90 min at 42° C. After reaction, RNA was degraded with 0.5N NaOH, and single-stranded cDNA was precipitated with ethanol. PCR amplification was carried out with one-tenth of the cDNA, 100 ng of each oligonucleotide primer (5'-TGCAAGCTTTCCACGACGGTGACACGCT-3' and 5-AGTGCAGGCCA–ACTTGTTCAGTGGA-3'), and 5 U of Taq polymerase in PCR buffer (50 mM KCl, 10 mM Tris-HCl, pH 8.3, 1.5 mM $MgCl_2$, and 0.001% gelatin) for 40 cycles in a programmable heat block (Ericomp, San Diego, Calif.). Each cycle included denaturation at 93° C. for 1 minute, reannealing at 62° for 80 seconds, and primer extension at 72° C. for 3 minutes. PCR products were extracted with phenol and precipitated with ethanol. The precipitate was dissolved in $H_2O$ and digested with restriction enzymes (Hind III and Sma 1). The p53 cDNA fragment was subcloned into virus vector to form Vp53B-Neo. Subcloned p53B was sequenced by using the dideoxy chain termination method (*Proc. Natl. Acad. Sci. U.S.A.* 74, 5463 (1977)).

The insert in one clone (designated p53B) was entirely sequenced (–1300 bp) to reveal a wild-type deduced amino acid sequence despite two silent nucleotide replacements (FIG. 1A). Another p53 cDNA clone (p53E), isolated from an epidermoid carcinoma cell line A431, was also sequenced, and was found to contain a point mutation at codon 273 that replaced Arg with His (FIG. 1A). This is a functionally significant mutation that has also been identified in p53 from two other tumor cell lines. In addition, a neutral sequence polymorphism in codon 72 (FIG. 1A) encoded either an Arg (p53B) or a Pro (p53E). This common amino acid polymorphism, which is without known functional significance, resulted in faster migration of p53B than p53E protein by SDS-PAGE, and was therefore exploited to distinguish between these proteins when they were coexpressed in the same cell.

p53E and p53B were then inserted into a Mo-MuLV-based retroviral vector containing neo as a selectable marker gene to form Vp53E-Neo and Vp53B-Neo viral genomes, respectively (FIG. 1B). In addition, to facilitate double replacement, Vp53B-Hygro was made by inserting p53B into a similar vector containing the gene which is known to confer resistance to hygromycin. Stocks of Vp53E-Neo, Vp53B-Neo and Vp53B-Hygro viruses were produced, utilizing conventional methods, with titers of about $1 \times 10^5$, $2\times10^4$, and $1\times10^5$, respectively. Expression of p53 proteins from the viruses was initially assessed in the murine NIH3T3-derived packaging line, PA12, that was used for virus production. Mutated and wild-type human p53 proteins were detected in their respective virus-producing cells, with the expected difference in migration by SDS-PAGE (FIG. 2A). Because spontaneous mutation of p53 may occur frequently in cultured cells, two additional biochemical properties of these p53 proteins were examined. These were their cellular half-lives, and their ability to bind to T antigen. p53B protein had a half-life of 20–30 minutes compared to 4 to 5 hours for p53E protein (FIG. 2B), consistent with published reports on the half-lives of wild-type and mutated p53 proteins. When virus-producing cells were transfected with a plasmid expressing large amounts of SV40T antigen, and lysates were immunoprecipitated with anti-p53 or anti-T antibodies, T antigen was coprecipitated with p53B but not p53E protein, indicating that only p53B protein could bind to T. These results together suggested that p53B-containing viruses expressed wild-type, and that p53E containing virus expressed mutated p53.

Expression of Exogeneous p53 in Osteosarcoma Cells.

Figure 3C:
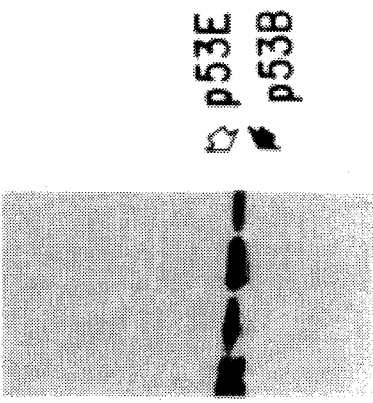
FIG. 3A, 3B and 3C depict the expression of human p53 proteins in virus-infected Saos-2 cells.
Figure 3B:
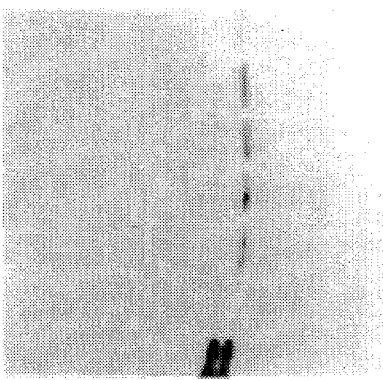
Figure 3A:
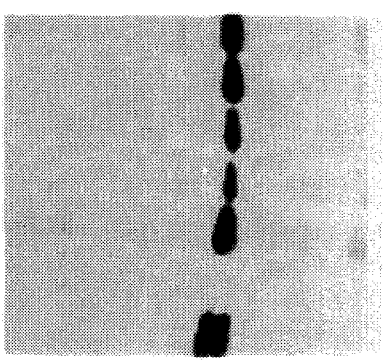

Osteosarcoma cell line Saos-2, which contains no endogenous p53, because of deletion of its gene, provides a clean background for functional studies of p53. In previous experiments, Saos-2 cells infected with parental viruses containing only neomycin- or hygromycin-resistance genes showed no changes in morphology and growth rate compared to uninfected cells, suggesting that drug selection did not have a significant influence on their neoplastic properties. Saos-2 cells infected with comparable titers of either Vp53E-Neo, Vp53B-Neo, or Vp53B-Hygro in the presence of the appropriate selective agent each yielded similar numbers of drug-resistant colonies. Most colonies could be individually propagated into mass cultures, with the notable observation that Vp53B-infected cells grew much more slowly than Vp53E-infected cells. Vp53E-infected clones uniformly expressed high levels of p53E protein (FIG. 3A). Of 30 Vp53B-infected clones examined, about 80% expressed detectable p53B protein (FIG. 3B). Two each of Vp53E-Neo and Vp53B-Hygro clones were randomly selected for a second infection by the other virus, and double-infected clones were isolated and propagated as above. These clones coexpressed both p53E and p53B protein (FIG. 3C). To again verify that p53B protein in these cells was not secondarily mutated, p53B-expressing clones were transfected with the SV40 antigen plasmid, and lysates immunoprecipitated as described above (FIG. 4). Anti-p53 antibody coprecipitated T in each clone, but anti-T antibody coprecipitated only p53B, even in cells expressing both p53B and p53E. The half-life of p53B in Saos-2 was also measured, and was similar to that of p53B in PA 12 cells. These data again support the notion that Vp53B-infected Saos-2 clones expressed wild-type p53.

Mutated p53 Conferred a Limited Growth Advantage to Saos-2 Cells in Culture.

Five randomly chosen clones that stably expressed p53E protein (p53EN-1 to 5) were compared to parental cells in terms of morphology (FIG. 5), growth rate (as doubling time, FIG. 6A), saturation density (FIG. 6B), soft-agar colony formation and tumorigenicity in nude mice were determined. In Tables 1 and 2, the results of soft-agar colony formation and tumorigenicity in nude mice, respectively are tabulated.

TABLE 1

Soft-agar colony formation of p53 virus-infected Saos-2 cells

| Virus-infected cells | Cell number seeded | | p53 expression |
|---|---|---|---|
| | $1.0 \times 10^5$ | $2.5 \times 10^4$ | |
| | Colony number | | |
| Parental | 392/388 | 104/76 | No |
| p53EN-1 | 928/968 | 396/372 | Mutated |
| p53EN-2 | 517/593 | 121/105 | Mutated |
| p53EN-3 | 485/534 | 96/123 | Mutated |
| p53EN-4 | 445/498 | 106/121 | Mutated |
| p53EN-5 | 582/441 | 132/172 | Mutated |
| p53BN-1 | <1/<1 | <1/<1 | Wild type |
| p53BN-2 | <1/<1 | <1/<1 | Wild type |
| p53BN-3 | <1/<1 | <1/<1 | Wild type |
| p53BN-4 | <1/<1 | <1/<1 | Wild type |
| p53BN-R | 414/384 | 54/48 | No |
| p53BH-1 | <1/<1 | <1/<1 | Wild type |
| p53BH-2 | <1/<1 | <1/<1 | Wild type |
| p53BH-3 | <1/<1 | <1/<1 | Wild type |
| p53EN-1-BH-1 | <1/<1 | <1/<1 | Mutated/Wild type |
| p53EN-1-BH-2 | <1/<1 | <1/<1 | Mutated/Wild type |
| p53EN-1-BH-3 | <1/<1 | <1/<1 | Mutated/Wild type |
| p53EN-2-BH-1 | <1/<1 | <1/<1 | Mutated/Wild type |
| p53EN-2-BH-2 | <1/<1 | <1/<1 | Mutated/Wild type |

TABLE 2

Tumorigenicity of p53 virus-infected Saos-2 cells

| Virus-infected cells | No of mice with tumor / No of mice injected | p53 expression |
|---|---|---|
| Parental | 10/10 | No |
| p53EN | 12/12 | Mutated |
| p53BN | 0/5 | Wild type |
| p53BH | 0/6 | Wild type |
| p53BN-R | 3/3 | No |
| p53EN-BH | 0/5 | Mutated/Wild type |

Figure 5B:
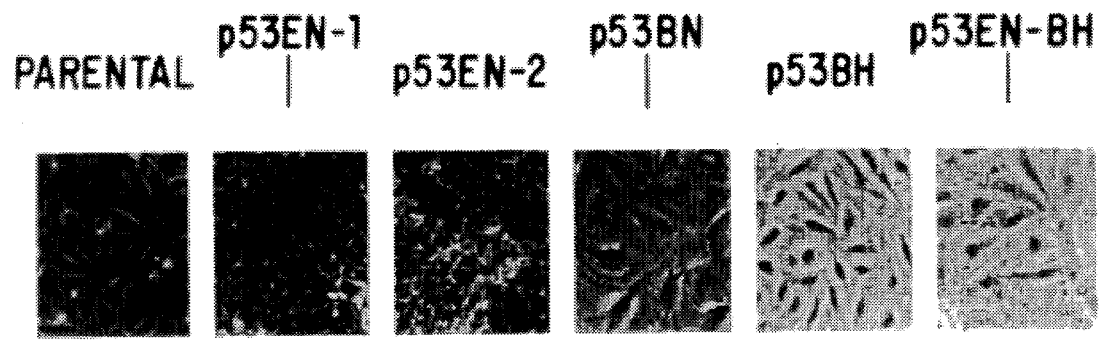

A difference in morphology was observed only under conditions of cell crowding, where cells of EN clones were far smaller and more refractile than parental cells (FIG. 5B). Correlatively, saturation density of the former was 4- to 5-fold greater than that of parental cells (FIG. 6B). This relative growth advantage was seen despite similar doubling times as measured under sparse growth conditions (FIG. 6A). Four EN clones and parental cells shared similar efficiencies in soft-agar colony formation (Table 1) and tumorigenicity in nude mice (Table 2). One clone, p53EN-1, had noticibly augmented abilities in both respects; in particular, it reliably formed large tumors from as few as $5\times10^5$ injected cells. This discrepancy was considered to be within the range of clonal variability expected among tumor cells. In summary, these results suggested that mutated p53 functioned in the absence of wild-type p53 to confer a limited growth advantage (higher saturation density) to Saos-2 cells in culture. In many other aspects of the neoplastic phenotype, the presence of point-mutated p53 was essentially equivalent to complete absence of p53.

Wild-type p53 Suppressed the Neoplastic Properties of Saos-2 Cells.

In comparison to parental Saos-2 cells, clones expressing p53B were invariably enlarged and flattened (FIG. 5), and had prolonged doubling times in culture of about 70 hours rather than 30–36 hours for parental or EN cells (FIG. 6A). Remarkably, the efficiency of soft-agar colony formation was reduced to less than the threshold for detecting a single colony, whereas parental cells and EN cells formed hundreds of colonies under the same conditions (Table 1). Injection of 1×10⁷ cells of each of seven p53B-expressing clones intom the flanks of nude mice resulted in the formation of no tumors after 8–10 weeks, even while the same number of parental or p53E-expressing cells formed tumors in all contralateral flanks (Table 2). These findings could not be explained by a peculiar effect of viral infection and selection because one clone, Vp53BN-R, derived from Vp53B-Neo-infected cells but lacking detectable expression of p53B, had a phenotype indistinguishable from parental cells (Tables 1 and 2). The ~50% reduction of growth rate of cultured Saos-2 cells by p53B was insufficient to account for the complete loss of tumorigenicity and soft-agar colony formation, implying that wild-type p53 specifically suppressed the neoplastic phenotype of these cells. These results suggested that loss of wild-type p53 was a significant event during the genesis of this tumor line, and, by extension, of other osteosarcomas, with mutated endogenous p53 genes. Wild-Type p53 Was Dominant to Mutated p53 In a Two-Allele Configuration.

Figure 7A:
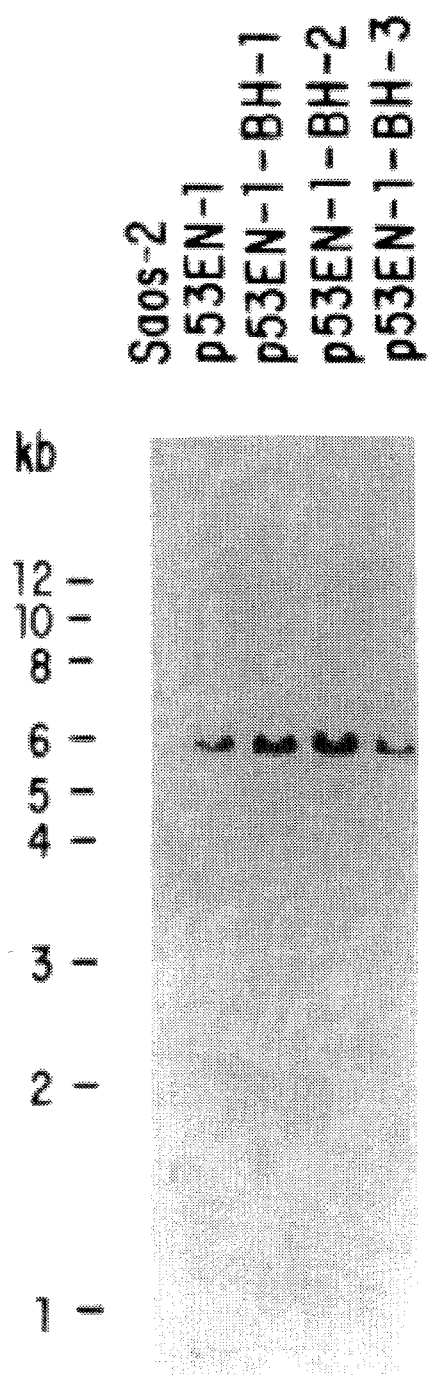
FIG. 7A is a Southern blot depicting the presence of a single integrated copy of Vp53E-Neo in p53EN-1 cells.
Figure 7B:
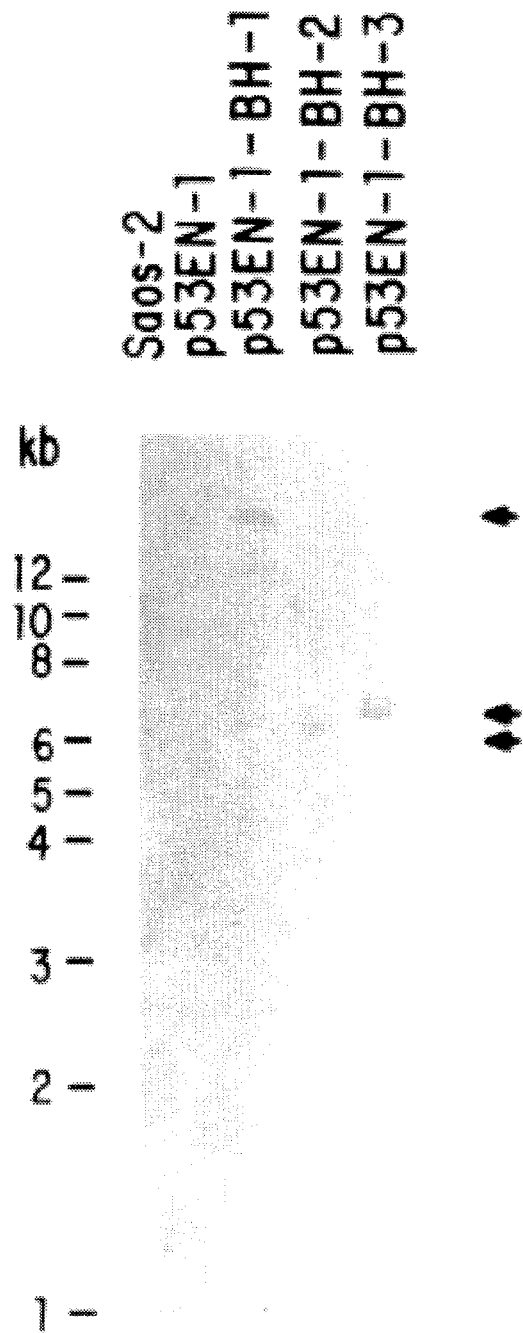
FIG. 7B is a Southern blot depicting single, independently integrated copies of Vp53B-Hygro in p53EN-BH clones.

Because both mutated and wild-type p53 proteins were apparently functional in Saos-2 cells, it was of interest to determine whether both activities could be simultaneously coexpressed, whether they cancelled out one another, or whether one activity was clearly dominant over the other. The configuration of one wild-type and one mutated allele was most relevant to natural human tumorigenesis, because this is a necessary intermediate step on the pathway toward complete loss of wild-type p53. Infection of two different p53E-expressing clones with Vp53B-Hygro yielded 22 hygromycin-resistant clones, of which 15 coexpressed both p53B and p53E. To determine the number of integrated copies of each virus present in these clones, genomic DNA of three clones derived from p53EN-1 cells infected with Vp53B-Hygro was analyzed by Southern blotting (FIG. 7). Hybridization with neo as a probe showed a single, common junctional fragment in all three clones, indicating the presence of a single integrated copy of Vp53E-Neo in p53EN-1 cells (FIG. 7A). Hybridization with hygro showed a single, unique junctional fragment in each clone, indicating the presence of single, independently integrated copies of Vp53B-Hygro in p53EN-BH clones (FIG. 7B). Single integrations were expected, based on previous use of a related recombinant retrovirus all comparable titers. These findings confirmed that p53EN-BH clones indeed contained one integrated copy of each virus, and that both exogenous p53 genes were expressed (FIG. 3). By criteria of morphology, growth rate, saturation density, soft-agar colony formation, and tumorigenicity in nude mice, double-replacement clones were indistinguishable from clones expressing only p53B (FIGS. 5 and 6, Tables 1 and 2). Cells obtained by infecting in the other order, i.e., p53B-expressing cells infected with Vp53E-Neo, had the same phenotype. Complete dominance of wild-type p53 activity was observed despite the ~10-fold lower quantities of wild-type than mutated p53 in these cells (FIG. 3). These results indicate that p53 can contribute to tumorigenesis only after loss of both wild-type alleles. They also indicate that restoration of wild-type p53 in tumor cells may have a suppressive effect, even in the presence of mutated p53 alleles.

Function of p53 as a Tumor Suppressor.

Introduction of wild-type p53 in human osteosarcoma cells lacking p53 expression clearly suppressed their neoplastic phenotype, indicating that p53 can function as a tumor suppressor gene in this system. Conversely, insertion of mutated p53 into these cells augmented one aspect of their growth in culture (saturation density), thereby showing that mutated p53 retains a limited function, albeit one that was overridden by wild-type p53. These results are broadly consistent with those of other investigators who have addressed the influence of wild-type murine p53 on oncogene-mediated transformation of primary rat embryo fibroblasts. In these studies, cotransfection of plasmid DNA containing the wild-type p53 gene markedly reduced the transformation efficiency of several activated oncogenes, either singly or in combinations such as ras+myc or ras+ E1A. Mutated p53 did not have this suppressive effect, and instead modestly boosted transformation efficiency. Wild-type p53 was also effective in reducing transformation by mutated p53 in concert with other oncogenes, suggesting "dominance" of the wild-type suppression function. Colonies recovered after transfection with wild-type p53 DNA either failed to express exogenous p53, or expressed only mutated p53.

Thus, it appeared that expression of exogenous, wild-type p53 was incompatible with formation of transformed colonies. These data suggested that wild-type murine p53 could function as a suppressor of transformed cells, although a nonspecific, toxic effect of wild-type p53 was not easily excluded. In contrast, in development of the present invention, transformed cells were utilized, and growing clones with altered phenotype that stably expressed oxogenous, wild-type p53 were obtained. These data in human cells, and the previous studies in mouse, together indicate that the tumor suppression function of p53 is a specific and fundamental property conserved across species boundaries.

The Nature of p53 Mutation.

It is known that murine p53 genes cloned from many cultured cell lines have point mutations that cluster in five conserved regions. This class of mutation was responsible for the initial impression that p53 was a dominant oncogene, because such p53 DNA fragments or constructs were active in promoting transformation of rodent cells in a variety of assays. Furthermore, protein products of mutated p53 genes have common antigenic and biochemical characteristics that differ from wild-type p53 protein, including a prolonged half-life that results in abnormally high cellular p53 protein levels. These features are quite reminiscent of other dominant oncogenes like *myc* and *ras*. On the other hand, gross deletions or rearrangements of the p53 gene, incompatible with expression of a gene product have been found in Friend-virus induced murine erythroleukemias, (*Nature* 314, 633–636 (1985)). Such mutations are considered to be characteristic of so-called tumor suppressor genes, and serve to inactivate their normal function. To explain how both kinds of mutation could impart the same oncogenic phenotype, it was proposed that wild-type p53 indeed functioned to suppress tumor formation, and that the many known point mutations of p53 actually served to inactivate this function. To explain the dominant transforming activity of mutated p53 genes in primary cells, it was necessary to hypothesize that mutated p53 protein somehow inactivated endogenous, wild-type p53 protein. This "dominant negative" effect might occur by inhibitory interactions between mutated and wild-type proteins, (*Nature*, 329, 219–222 (1987)). Further interpretation of these studies was limited by the technical drawbacks of transfection, and by the uncertain role of endogenous p53 in primary cells.

In the human system, Vogelstein and colleagues have shown in elegant studies that deletions and point mutations of p53 can coexist in colorectal, lung or breast carcinomas. Loss of heterozygosity of polymorphic markers in chromosome region 17p is seen frequently in these tumors, corresponding to the loss of one copy of the p53 gene (by deletion or mitotic nondisjunction). The remaining p53 allele is often affected by somatic point mutations in conserved regions. The end result is the loss of both wild-type p53 alleles from tumor cells. The same loss also occurs in human osteosarcomas and hepatocellular carcinomas by deletion of both p53 alleles. Complete loss of wild-type alleles is highly analogous to findings with the retinoblastoma gene, and support the idea that p53 is a tumor suppressor gene. However, Nigro et al., J. M. Nigro et al., *Nature* 342, 705–708 (1989), described one colorectal carcinoma coexpressing both mutated ($Asp^{281} \rightarrow Gly$) and wild-type p53 alleles. The existence of this tumor was interpreted as favoring an oncogenic activity of a single mutated p53 allele in the presence of wild-type p53; loss of the second, wild-type allele would contribute to progression of the tumor.

In the present invention, it has been found that the phenotype of Saos-2 cells with single copies of wild-type and mutated p53 alleles was indistinguishable from cells expressing wild-type p53 alone, suggesting that wild-type p53 is dominant to mutated p53 in two-allele configuration. Given this result, other explanations for the discrepant colon carcinoma case may be considered: 1) an intermediate stage of p53 mutation was coincidentally captured, and p53 had not yet contributed to the neoplastic properties of this tumor; and 2) the "wild-type" p53 allele in this tumor actually carried a functionally important mutation outside of the region sequenced (exons 5–9). On the other hand, it is possible that certain mutated p53 alleles behave differently than others, or that mutated p53 alleles function differently in other types of tumor cells than in our model Saos-2 system. These possibilities can be addressed by replicating experiments with other mutated p53 genes and other p53-negative cells.

Confusion in previous studies about the interaction between wild-type and mutated p53 have clouded an essential question: is mutated p53 completely functionless, i.e., is it equivalent to its complete deletion, or does it retains some limited function? It is concluded that the latter case is more probable. A single copy of mutated p53 increased in saturation density of Saos-2 cells, and of course this effect could not be mediated by inactivation of endogenous p53. Similarly, Wolf et al., (*Cell* 38,119–126 (1984)), introduced what was probably a mutated p53 gene into AB-MuLV-transformed murine cells that lacked endogenous p53 expression, and found that their oncogenic potential was increased. Therefore, mutated p53 alleles may confer a growth advantage or a more malignant phenotype in vivo to tumor cells without wild-type p53.

The findings that mutated p53 has a biological function, and that its function is recessive to that of wild-type p53, are inconsistent with the hypothesis of a dominant negative effect, at least as it applies in natural human tumorigenesis. The dominant transforming properties of mutated murine p53 alleles may be due to the high copy numbers of genes introduced by transfection, and the resulting massive overexpression of mutated p53. Under these circumstances, even its limited intrinsic activity may be sufficient to contribute to a transformed phenotype.

Mechanisms of p53 Function.

The physiological or biochemical functions of p53 are now known with certainty. In nontransformed cells, p53 synthesis and mRNA transcription increase dramatically during the transition from $G_0/G_1$ to S phase, indirectly suggesting a role in cell cycle regulation. Recent evidence also points to a possibly related activity in regulating DNA replication. Studies on suppression of the neoplastic phenotype may provide general parameters for understanding the normal function of p53. It is clear, for example, that p53 is not required for progression of the cell cycle, nor is its presence necessarily preventive of cell growth and division. Therefore, it may participate in regulation of these basic cellular processes in response to external growth or differentiation signals. Wild-type and mutated p53 can differ by a single amino acid yet have opposing functions in the cell. Under conditions of equal gene dosage, wild-type p53 is able to override the influence of mutated p53 despite a 10-fold molar excess of the latter. These observations may be explained by competition of wild-type and mutated p53 for common cellular targets, for which wild-type p53 is much more avid. In this model, wild-type and mutated p53 would transmit opposite growth signals to these targets, with total absence of p53 perhaps an intermediate signal. Alternatively, mutated p53 may act in an independent pathway to promote selective features of the neoplastic phenotype.

Genetic Mechanisms of p53 Inactivation.

The dominance of wild-type over mutated p53 in a two-allele configuration implies that both wild-type p53 alleles must be lost for an oncogenic effect. In this respect, p53 conforms to a model of tumor suppressor gene inactivation that can be understood in the case of the retinoblastoma gene. In this regard, reference may be made to pending applications Retinoblastoma Gene Cancer Suppressing and Regulator, Ser. No. 108,748, filed Oct. 15, 1987 and Suppression of the Neoplastic Phenotype, Ser. No. 265,829, filed Oct. 31, 1988. Complete loss of the RB gene product is so far universal in retinoblastomas, and wild-type and mutated RB alleles have not been observed to coexist in tumor cells. These findings suggest that RB contributes to oncogenesis only after its complete inactivation. On the other hand, many tumor cells have normal RB expression, and are neoplastic presumably because of mutations in other genes. In such RB+tumor cells, introduction of additional, exogenous RB may have little or no effect; for example, it has been found that RB+U2OS osteosarcoma cell lines with wild-type p53 alleles are not known to exist. The results obtained to date indicate that p53 has broad suppression activity in several types of human tumors. Thus, the suppression effect of exogenous RB or p53 may occur only in tumor cells with inactivated RB or p53 genes. These shared properties of RB and p53 reinforce the tumor suppressor gene concept, including the possible clinical utility of their replacement in appropriate tumor cells.

Summary.

Mutations of the gene encoding p53, a 53 kD cellular protein, are found frequently in human tumor cells, suggesting a crucial role for this gene in human oncogenesis. In order to model the stepwise mutation or loss of both p53 alleles during human oncogenesis, a human osteosarcoma cell line, Saos-2 was utilized that lacked endogenous p53 due to complete deletion of the gene. Single copies of exogenous p53 genes were then introduced by infecting cells with recombinant retroviruses containing either wild-type or point-mutated versions of the p53 cDNA sequence. It was found that 1) expression of wild-type p53 suppresses the neoplastic phenotype of Saos-2 cells; 2) expression of mutated p53 confers a limited growth advantage to cells in the absence of wild-type p53; and 3) wild-type p53 is phenotypically dominant to mutated p53 in a two-allele configuration. These results indicate that, as with the retinoblastoma gene, mutation of both alleles of the p53 gene is essential for its role in oncogenesis.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

What is claimed is:

1. A method of treating mammalian cancer cells lacking endogenous wild-type p53 protein, comprising introducing a wild-type p53 tumor suppressor gene encoding said endogenous wild-type p53 protein into said mammalian cancer cells, whereby said mammalian cancer cells' neoplastic phenotype is suppressed.

2. A method of treating mammalian cancer cells lacking endogenous wild-type p53 protein, comprising introducing into said mammalian cancer cells a wild-type p53 tumor suppressor gene derived from the same mammalian species as said mammalian cancer cells, whereby said mammalian cancer cells' neoplastic phenotype is suppressed.

3. The method of claim 1 or 2, wherein the mammalian cancer cell having no endogenous wild-type p53 protein lacks the wild-type p53 tumor suppressor gene.

4. The method of claim 1 or 2, wherein the mammalian cancer cell having no endogenous wild-type p53 protein has a mutated p53 tumor suppressor gene.

5. The method of claim 1 or 2, wherein the introduction of the wild-type p53 tumor suppressor gene is by retroviral infection.

6. The method of claim 1 or 2, wherein the mammalian cancer cell is an osteosarcoma cell, lung carcinoma cell, lymphoma cell, leukemia cell, soft-tissue sarcoma cell, breast carcinoma cell, bladder carcinoma cell or prostate carcinoma cell.

* * * * *

UNITED STATES PATENT AND TRADEMARK OFFICE
CERTIFICATE OF CORRECTION

PATENT NO. : 5,532,220

DATED : July 2, 1996

INVENTOR(S) : Wen-Hwa Lee and Phang-Lang Chen

It is certified that error appears in the above-identified patent and that said Letters Patent is hereby corrected as shown below:
On the title page item [60]:

In Related U.S. Application Data

Please delete "and a continuation-in-part of Ser. No. 533,892, Jul. 16, 1990, Pat. No. 5,104,571" and substitute therefor --and a continuation-in-part of Ser. No. 553,892, abandoned--.

Signed and Sealed this

Seventh Day of October, 1997

*Attest:*

BRUCE LEHMAN

*Attesting Officer*     Commissioner of Patents and Trademarks